United States Patent [19]

Lewis et al.

[11] 4,233,168

[45] * Nov. 11, 1980

[54] LUBRICANT COMPOSITIONS CONTAINING DISPERSANT ADDITIVES

[75] Inventors: Robert A. Lewis, Berkeley; Lewis R. Honnen, Petaluma, both of Calif.

[73] Assignee: Chevron Research Company, San Francisco, Calif.

[*] Notice: The portion of the term of this patent subsequent to Jul. 10, 1996, has been disclaimed.

[21] Appl. No.: 917,426

[22] Filed: Jun. 19, 1978

Related U.S. Application Data

[63] Continuation-in-part of Ser. No. 887,703, Mar. 17, 1978, abandoned, which is a continuation-in-part of Ser. No. 801,441, May 27, 1977, Pat. No. 4,160,648, which is a continuation-in-part of Ser. No. 730,495, Oct. 7, 1976, abandoned, which is a continuation-in-part of Ser. No. 700,922, Jun. 29, 1976, abandoned, which is a continuation-in-part of Ser. No. 698,243, Jun. 21, 1976, abandoned.

[51] Int. Cl.[3] .................. C07C 125/06; C07D 295/14; C10M 1/32

[52] U.S. Cl. .......................... 252/51.5 A; 252/51.5 R; 260/239 BC; 544/398; 544/402; 548/320; 560/158; 560/159

[58] Field of Search ..................... 252/51.5 R, 51.5 A; 560/158, 159; 260/239 AL, 239 BC; 544/398, 402; 548/320

[56] References Cited

U.S. PATENT DOCUMENTS

| | | | |
|---|---|---|---|
| 2,991,162 | 7/1961 | Malec | 44/71 X |
| 3,359,303 | 12/1967 | Coker et al. | 560/159 |
| 3,438,757 | 4/1969 | Honnen et al. | 44/58 |
| 3,454,625 | 7/1969 | Eiseman, Jr. et al. | 560/159 |
| 3,565,592 | 2/1971 | Mehmedbasich | 44/71 X |
| 3,630,904 | 12/1971 | Musser et al. | 252/51.5 A |
| 3,652,240 | 3/1972 | Dorn et al. | 44/71 X |
| 3,658,882 | 4/1972 | Eiseman, Jr. | 260/463 X |
| 3,671,511 | 6/1972 | Honnen et al. | 44/58 X |
| 3,786,081 | 1/1974 | Oppenlaender et al. | 560/158 X |
| 3,813,341 | 5/1974 | Elliott et al. | 560/158 X |
| 3,836,470 | 9/1974 | Miller | 252/51.5 A |
| 3,960,515 | 6/1976 | Honnen | 44/63 X |
| 4,160,648 | 7/1979 | Lewis et al. | 44/71 X |

FOREIGN PATENT DOCUMENTS 855962 7/1977 Belgium .

*Primary Examiner*—Thomas A. Waltz
*Attorney, Agent, or Firm*—D. A. Newell; S. R. LaPaglia

[57] ABSTRACT

Lubricant compositions for internal combustion engines are provided containing dispersant additives which prevent sludge and varnish formation in the crankcase. The additives are oil-soluble poly(oxyalkylene) aminocarbamates comprising a hydrocarbyl-terminated poly(oxyalkylene) chain of 2-5 carbon oxyalkylene units.

24 Claims, No Drawings

LUBRICANT COMPOSITIONS CONTAINING DISPERSANT ADDITIVES

CROSS REFERENCE TO RELATED APPLICATIONS

This is a continuation-in-part of U.S. application Ser. No. 887,703, filed Mar. 17, 1978 (now abandoned), of Robert A. Lewis and Lewis R. Honnen, which in turn is a continuation-in-part of Ser. No. 801,441, filed May 27, 1977 (now issued as U.S. Pat. No. 4,160,648), which in turn is a continuation-in-part of Ser. No. 730,495, filed Oct. 7, 1976 (now abandoned), which in turn is a continuation-in-part of Ser. No. 700,922, filed June 29, 1976 (now abandoned), which in turn is a continuation-in-part of Ser. No. 698,243, filed June 21, 1976 (now abandoned).

BACKGROUND OF THE INVENTION

1. Field of the Invention

This application relates to lubricating oil compositions containing poly(oxyalkylene) aminocarbamates which contribute dispersancy and detergency to the compositions.

Lubricating oil compositions, particularly for use in internal combustion engines, have long performed many functions other than simply lubricating moving parts. Modern-day, highly compounded lubricating oil compositions provide anti-wear, anti-oxidant, extreme-pressure and anti-rust protection in addition to maintaining the cleanliness of the engine by detergency and dispersancy. Many lubricating oil additives are well known for accomplishing these functions. For maintaining engine cleanliness, a well-known class of ashless detergents which have been found to be particularly useful are the amine reaction products of hydrocarbyl-substituted succinic acids, i.e., the well-known succinimides. It is known that most previously employed lubricating oil dispersancy additives, such as the alkenyl succinimides, during engine operation cause deposits to form in the combustion chambers of the engines. Belgium Pat. No. 855,962, a counterpart of U.S. Patent applications Ser. Nos. 698,243; 700,922; 730,495 (all abandoned) and Ser. No. 801,441 now U.S. Pat. No. 4,160,648 discloses and claims fuel compositions containing certain poly(oxyalkylene) aminocarbamates as deposit control additives. While, in general, deposit control additives are not believed to be useful dispersants for lubricating oil compositions, certain aminocarbamates are useful in this regard.

SUMMARY OF THE INVENTION

It has been found that improved lubricating oil compositions comprise a major amount of an oil of lubricating viscosity and an amount sufficient to provide dispersancy of hydrocarbylpoly(oxyalkylene) aminocarbamate of molecular weight from about 600 to about 10,000 and having at least one basic nitrogen atom; wherein said poly(oxyalkylene) moiety is composed of oxyalkylene units selected from 2 to 5 carbon oxyalkylene units and containing at least sufficient branched chain oxyalkylene units to render said carbamate soluble in said lubricating oil composition; and said hydrocarbyl group contains from 1 to about 30 carbon atoms.

DETAILED DESCRIPTION OF THE INVENTION

The poly(oxyalkylene) aminocarbamate of the present invention consists of an amine moiety and a poly(oxyalkylene) moiety comprising at least one hydrocarbyl-terminated poly(oxyalkylene) polymer bonded through a carbamate linkage, i.e., $$-OC(O)\overset{|}{N}-.$$

The amine component of the carbamate and the poly(oxyalkylene) component of the carbamate are selected to provide solubility in the lubricating oil composition and dispersancy.

AMINE COMPONENT

The amine moiety of the hydrocarbyl-terminated poly(oxyalkylene) aminocarbamate is preferably derived from a polyamine having from 2 to about 12 amine nitrogen atoms and from 2 to about 40 carbon atoms. The polyamine is preferably reacted with a hydrocarbylpoly(oxyalkylene) chloroformate to produce the hydrocarbylpoly(oxyalkylene) aminocarbamate lubricating oil additive finding use within the scope of the present invention. The chloroformate is itself derived from hydrocarbylpoly(oxyalkylene) alcohol by reaction with phosgene. The polyamine, encompassing diamines, provides the product poly(oxyalkylene) aminocarbamate with, on the average, at least about one basic nitrogen atom per carbamate molecule, i.e., a nitrogen atom titratable by a strong acid. The polyamine preferably has a carbon-to-nitrogen ratio of from about 1:1 to about 10:1.

The polyamine may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like lower alkyl or lower alkoxy, means a group containing from 1 to about 6 carbon atoms. At least one of the substituents on one of the basic nitrogen atoms of the polyamine is hydrogen, e.g., at least one of the basic nitrogen atoms of the polyamine is a primary or secondary amino nitrogen.

Hydrocarbyl, as used in describing all the components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxy-isopropyl, 4-hydroxybutyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, diethyleneoxymethyl, triethyleneoxyethyl, tetraethyleneoxyethyl, diethyleneoxyhexyl, etc. The aforementioned acyl groups (C) are such as propionyl, acetyl, etc. The more preferred substituents are hydrogen, $C_1$–$C_6$ alkyls and $C_1$–$C_6$ hydroxyalkyls.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and poly-substituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl and hydroxyalkyl-substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethyl-propylene, trimethylene, 1,3,2-hydroxypropylene, etc. Examples of such polyamines include ethylene diamine, diethylene triamine, di(trimethylene)triamine, dipropylene triamine, triethylene tetraamine, tripropylene tetraamine, tetraethylene pentamine, and pentaethylene hexamine. Such amines encompass isomers such as branched-chain polyamines and the previously-mentioned substituted polyamines, including hydroxy- and hydrocarbyl-substituted polyamines. Among the polyalkylene polyamines, those containing 2–12 amino nitrogen atoms and 2–24 carbon atoms are especially preferred, and the $C_2$–$C_3$ alkylene polyamines are most preferred, in particular, the lower polyalkylene polyamines, e.g., ethylene diamine, dipropylene triamine, etc.

The amine component of the poly(oxyalkylene) aminocarbamate also may be derived from heterocyclic polyamines, heterocyclic substituted amines and substituted heterocyclic compounds, wherein the heterocycle comprises one or more 5–6 membered rings containing oxygen and/or nitrogen. Such heterocyclic rings may be saturated or unsaturated and substituted with groups selected from the aforementioned (A), (B), (C) and (D). The heterocyclic compounds are exemplified by piperazines, such as 2-methylpiperazine, N-(2-hydroxyethyl)-piperazine, 1,2-bis-(N-piperazinyl)ethane and N,N'-bis(N-piperazinyl)piperazine, 2-methyl-imidazoline, 3-amino-piperidine, 3-aminopyridine, N-(3-aminopropyl)-morpholine, etc. Among the heterocyclic compounds, the piperazines are preferred.

Typical polyamines that can be used to form the compounds of this invention by reaction with a poly(oxyalkylene) chloroformate include the following: ethylene diamine, 1,2-propylene diamine, 1,3-propylene diamine, diethylene triamine, triethylene tetraamine, hexamethylene diamine, tetraethylene pentamine, dimethylaminopropylene diamine, N-(beta-aminoethyl)piperazine, N-(beta-aminoethyl)piperidine, 3-amino-N-ethylpiperidine, N-(beta-aminoethyl)morpholine, N,N'-di(beta-aminoethyl)piperazine, N,N'-di(beta-aminoethyl)imidazolidone-2, N-(beta-cyanoethyl)ethane-1,2-diamine, 1-amino-3,6,9-triazaoctadecane, 1-amino-3,6-diaza-9-oxadecane, N-(beta-aminoethyl)diethanolamine, N'-acetylmethyl-N-(beta-aminoethyl)ethane-1,2-diamine, N-acetonyl-1,2-propanediamine, N-(beta-nitroethyl)-1,3-propane diamine, 1,3-dimethyl-5-(beta-aminoethyl)hexahydrotriazine, N-(beta-aminoethyl)-hexahydrotriazine, 5-(beta-aminoethyl)-1,3,5-dioxazine, 2-(2-aminoethylamino)-ethanol, 2-[2-(2-aminoethylamino)ethylamino]-ethanol.

The amine component of the poly(oxyalkylene) aminocarbamate may also be derived from an amine-containing compound which is capable of reacting with a hydrocarbylpoly(oxyalkylene) alcohol to produce a hydrocarbylpoly(oxyalkylene) aminocarbamate having at least one residual basic nitrogen atom. For example, a substituted aminoisocyanate, such as $(R)_2NCH_2CH_2NCO$, wherein R is, for example, a hydrocarbyl group, reacts with the alcohol to produce the aminocarbamate additive finding use within the scope of the present invention. Typical aminoisocyanates that may be used to form the lubricating oil additive compounds of this invention by reaction with a hydrocarbylpoly(oxyalkylene) alcohol include the following: N,N-(dimethyl)aminoisocyanatoethane, generally, N,N-(dihydrocarbyl)aminoisocyanatoalkane, more generally, N-(perhydrocarbyl)isocyanatopolyalkylene polyamine, N,N-(dimethyl)aminoisocyanatobenzene, etc.

In many instances the amine used as a reactant in the production of the carbamate of the present invention is not a single compound but a mixture in which one or several compounds predominate with the average composition indicated. For example, tetraethylene pentamine prepared by the polymerization of aziridine or the reaction of dichloroethylene and ammonia will have both lower and higher amine members, e.g., triethylene tetraamine, substituted piperazines and pentaethylene hexamine, but the composition will be mainly tetraethylene pentamine and the empirical formula of the total amine composition will closely approximate that of tetraethylene pentamine. Finally, in preparing the compounds of this invention, where the various nitrogen atoms of the polyamine are not geometrically equivalent, several substitutional isomers are possible and are encompassed within the final product. Methods of preparation of amines, isocyanates and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volume 2, pp. 99–116.

POLY(OXYALKYLENE) COMPONENT

The hydrocarbyl-terminated poly(oxyalkylene) polymers which are utilized in preparing the carbamates of the present invention are monohydroxy compounds, i.e., alcohols, often termed monohydroxy polyethers, or "capped" poly(oxyalkylene) glycols and are to be distinguished from the poly(oxyalkylene) glycols (diols), or polyols, which are not hydrocarbyl-terminated, i.e., not capped. The hydrocarbyl-terminated poly(oxyalkylene) alcohols are produced by the addition of lower alkylene oxides, such as oxirane, ethylene oxide, propylene oxide, the butylene oxides, or the pentylene oxides to the hydroxy compound ROH under polymerization conditions. Methods of production and properties of these polymers are disclosed in U.S. Pat. Nos. 2,841,479 and 2,782,240, and the aforementioned Kirk-Othmer's "Encyclopedia of Chemical Technology", Volume 19, p. 507. In the polymerization reaction a single type of alkylene oxide may be employed, e.g., propylene oxide, in which case the product is a homopolymer, e.g., a poly(oxypropylene) propanol. However, copolymers are equally satisfactory and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene) polymers for the practice of the present invention. Random polymers are more easily prepared when the reactivities of the oxides are relatively equal. In certain cases, when ethylene oxide is copolymerized with other oxides, the higher reaction rate of ethylene oxide makes the preparation of random copolymers difficult. In either case, block copolymers can be prepared. Block copolymers are prepared by contacting the hydroxyl-containing compound with first one alkylene oxide, then the others in any order, or repetitively, under polymerization conditions. A particular block copolymer is represented by a polymer prepared by polymerizing propylene oxide on a suitable monohydroxy compound to form a poly(oxypropylene) alcohol and then polymerizing butylene oxide on the poly(oxypropylene) alcohol.

In general, the poly(oxyalkylene) polymers are mixtures of compounds that differ in polymer chain length. However, their properties closely approximate those of the polymer represented by the average composition and molecular weight.

The hydrocarbylpoly(oxyalkylene) moiety of the carbamate consists of one or more hydrocarbyl-terminated poly(oxyalkylene) polymers composed of oxyalkylene units containing from 2 to about 5 carbon atoms. The polymers are bound to the aminocarbamate via carbamate linkages, and the poly(oxyalkylene) moiety consists of at least one such poly(oxyalkylene) polymer. The hydrocarbyl group contains from 1 to about 30 carbon atoms, preferably from 2 to about 20 carbon atoms. Preferably the oxyalkylene units contain from 3 to 4 carbon atoms and the molecular weight of the hydrocarbylpoly(oxyalkylene) moiety is from about 500 to about 10,000, more preferably from about 500 to about 5,000. Each poly(oxyalkylene) polymer contains at least about 5 oxyalkylene units, preferably 8 to about 100 oxyalkylene units, more preferably about 10–100 units and most preferably 10 to about 25 such units. In general, the oxyalkylene units may be branched or unbranched. Preferably the poly(oxyalkylene) polymer chain contains at least some $C_3$–$C_5$ oxyalkylene units, more preferably, branched $C_3$–$C_5$ oxyalkylene units are present in at least sufficient number to render the hydrocarbyl-terminated poly(oxyalkylene) aminocarbamate soluble in the lubricating oil composition of the present invention. This solubility condition is satisfied if the carbamate is soluble in hydrocarbons of lubricating viscosity, i.e., about 35–50,000 SUS, at 100° F., at least to the extent of about 0.01 percent by weight. A poly(oxyalkylene) polymer chain composed of branched three and/or four carbon oxyalkylene units in at least sufficient amount to effect solubility in the lube composition is most preferred. The structures of the $C_3$–$C_5$ oxyalkylene units are any of the isomeric structures well known to the organic chemist, e.g., n-propylene, $—CH_2CH_2CH_2—$; isopropylene, $—C(CH_3)CH_2—$; n-butylene, $—CH_2CH_2CH_2CH_2—$; sec.-butylene, $—CH(CH_2CH_3)CH_2—$; tert.-butylene, $—C(CH_3)_2CH_2—$; disec.-butylene, $—CH(CH_3)CH(CH_3)—$; isobutylene, $—CH_2CH(CH_3)CH_2—$; etc. The preferred poly(oxyalkylene) compounds are composed, at least in part, of the branched oxyalkylene isomers, particularly oxy(isopropylene), and oxy(sec.-butylene) units which are obtained from 1,2-propylene oxide and from 1,2-butylene oxide, respectively.

The hydrocarbyl moiety (R-) which terminates the poly(oxyalkylene) chain contains from 1 to about 30 carbon atoms, preferably from 2 to about 20 carbon atoms, and is generally derived from the monohydroxy compound (ROH) which is the initial site of the alkylene oxide addition in the polymerization reaction. Such monohydroxy compounds are preferably aliphatic or aromatic alcohols of from 1 to about 30 carbon atoms, more preferably an alkanol or an alkylphenol, and most preferably an alkylphenol wherein the alkyl is a straight or branched chain of from 1 to about 24 carbon atoms. One such preferred alkyl group is obtained by polymerizing propylene to an average of 4 units and has the common name of propylene tetramer. The preferred material may be termed either an alkylphenylpoly(oxyalkylene) alcohol or a polyalkoxylated alkylphenol.

HYDROCARBYLPOLY(OXYALKYLENE) AMINOCARBAMATE

Having described the amine component and the poly(oxyalkylene) component, the poly(oxyalkylene) aminocarbamate lubricating oil additive of the present invention is obtained by linking these components together through a carbamate linkage, i.e., $$—O—C(O)—\overset{|}{N}—,$$

wherein the oxygen is the terminal hydroxyl oxygen of the poly(oxyalkylene) alcohol component, and the carbonyl group, —C(O)—, is preferably provided by a coupling agent, e.g., phosgene. In the preferred method of preparation, the hydrocarbylpoly(oxyalkylene) alcohol is reacted with phosgene to produce a hydrocarbylpoly(oxyalkylene) chloroformate. The chloroformate is reacted with a polyamine. The carbamate linkages are formed as the poly(oxyalkylene) chains are bound to the nitrogen of the polyamine through the oxycarbonyl group (—O—C(O)—) of the chloroformate. Since there may be more than one nitrogen atom of the polyamine which is capable of reacting with the chloroformate, the hydrocarbylpoly(oxyalkylene) aminocarbamate contains at least one hydrocarbylpoly(oxyalkylene) polymer chain bonded through an oxycarbonyl group to a nitrogen atom of the polyamine, but the carbamate may contain from 1 to 2 or more such chains. It is preferred that the hydrocarbylpoly(oxyalkylene) aminocarbamate product contain, on the average, about 1 poly(oxyalkylene) chain per molecule (monocarbamate), although it is understood that this reaction route may lead to mixtures containing appreciable amounts of di- or higher poly(oxyalkylene) chain substitution on a polyamine containing several reactive nitrogen atoms (dicarbamate or higher degree of substitution). To avert di- or higher substitution on the polyamine, a large excess of polyamine may be contacted with the chloroformate. Alternatively, a monoisocyanato-substituted amine may be reacted directly with the poly(oxyalkylene) alcohol. The dicarbamate produced by the reaction of a polyamine with two molecules of hydrocarbylpoly(oxyalkylene) chloroformate is to be distinguished from the dicarbamate produced by the reaction of a poly(oxyalkylene) di(chloroformate) with two mols of the same polyamine. For purposes of distinction, the latter dicarbamate will be called the "bis(aminocarbamate)", and the former simply "dicarbamate". The bis-(aminocarbamate), i.e., that derived from a poly(oxyalkylene) glycol, is not thought to be as effective in lubricating oil compositions.

The hydrocarbylpoly(oxyalkylene) aminocarbamate finding use within the scope of the present invention is characterized by having at least about one basic nitrogen atom per molecule. Since, within the compositional mixture, the amine moiety may contain more or less nitrogen, and consequently the poly(oxyalkylene) moiety of the carbamate may contain more than one poly-(oxyalkylene) polymer, the aminocarbamate is further characterized by having, on the average, at least one basic nitrogen atom per aminocarbamate molecule. A "basic nitrogen atom" is one that is titratable by a strong acid, e.g., a primary, secondary or tertiary amino nitrogen, as distinguished from, for example, amido nitrogens,

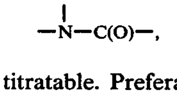

which are not so titratable. Preferably, at least one of the basic nitrogen atoms is in a primary or secondary amino group.

The preferred hydrocarbylpoly(oxyalkylene) aminocarbamate has a molecular weight of from about 600 to about 10,000 (representing an average maximum disubstitution of poly(oxyalkylene) polymer in the carbamate) and more preferably from about 1,200 to about 5,000.

A class of preferred carbamates may be described by the following general formula:

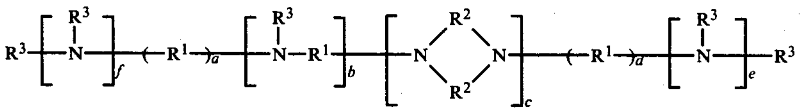

wherein two $R^3$ groups attached to the same nitrogen atom may form a 5- or 6-membered saturated or unsaturated nitrogen heterocyclic radical, such as pyrrolyl, pyrrolidinyl, imidazolidinyl, oxazolidinyl, pyrrolinyl, imidazolinyl, piperidino, piperazinyl, isoxazolyl, hexahydrotriazinyl, morpholino, etc.; wherein said heterocyclic radical may be substituted with substituents selected from the aforementioned (A), (B), (C) and (D) groups of substituents. The remaining $R^3$ groups are the same or different substituents selected from the aforementioned (A), (B), (C) and (D) groups of substituents and a poly(oxyalkylene) oxycarbonyl group of the formula $R-(OC_gH_{2g})_jO-C(O)-$ in which g is an integer of 2 to 5; j is an integer such that the molecular weight of the poly(oxyalkylene) group is from about 500 to about 5,000, i.e., j is at least about 5 and preferably from 8 to about 100, and R is a hydrocarbyl group of from 1 to 30 carbon atoms. $R^1$ is the same or different alkylene, carbonyl, oxycarbonyl, or hydroxy-substituted alkylene radical of from 2 to 6 carbon atoms, $R^2$ is carbonyl, alkylene carbonyl or alkylene of from 2 to 4 carbon atoms with vicinal linkages. At least one, and preferably no more than one, of the $R^3$ groups is the poly(oxyalkylene) oxycarbonyl group, and a sufficent number of the oxyalkylene units, $-(OC_gH_{2g})-$, are branched $C_3$–$C_5$ oxyalkylene units to render the compound soluble in the lubricating oil composition. $R^3$, $R^1$, and $R^2$ are selected such that at least one nitrogen atom is a basic nitrogen atom, i.e., titratable with strong acid. a is 0 or 1, preferably 1; b is an integer from 0 to 4, preferably 0 to 2; c is 0 or 1, preferably 0; d is 0 or 1, preferably 0; e is 0 or 1, preferably 1; and f is 0 or 1, and equal to 1 when c is 0. It is also provided that the sum of $f+b+2c+e$ is equal to or greater than 2.

PREPARATION OF THE POLY(OXYALKYLENE) AMINOCARBAMATES

The additives of this invention may be most conveniently prepared, as has been previously noted, by reaction of phosgene with the monohydroxy poly(oxyalkylene) compound followed by reaction of the product with a suitable amine.

Bis(aminocarbamates) formed by reacting phosgene with an "uncapped" poly(oxyalkylene) diol followed by reaction with polyamine are believed to have lower dispersant activity.

The reaction of the poly(oxyalkylene) compound and phosgene is usually carried out on an essentially equimolar basis, although excess phosgene can be used to improve the degree of reaction. The reaction may be carried out at temperatures from −10° to 100° C., preferably in the range of 0° to 50° C. The reaction will usually be complete within ¼ to 5 hours. Times of reaction will usually be in the range of from 2 to 4 hours.

A solvent may be used in the chloroformylation reaction. Suitable solvents include benzene, toluene, etc.

The reaction of the resultant chloroformate with the amine may be carried out neat or preferably in solution. Temperatures of from −10° to 200° C. may be utilized. The desired product may be obtained by water wash and stripping, usually by the aid of vacuum, of any residual solvent.

The mol ratio of the basic amine nitrogen to polyether chloroformate will generally be in the range from about 2 to 20 mols of basic amine nitrogen per mol of chloroformate, and more usually 5 to 15 mols of basic amine nitrogen per mol of chloroformate. The mol ratio will depend upon the particular amine and the desired ratio of polyether to amine. Since suppression of polysubstitution of the alkylene polyamines is usually desired, large mol excesses of the amine will be used. For example, preparation of the aminocarbamate from ethylenediamine with an ethylenediamine to chloroformate ratio of 2.5 to 1 has yielded a basic nitrogen to total nitrogen ratio in the product of 0.27, whereas raising the ethylene diamine to chloroformate ratio to 9.1 to 1 gives 0.42 basic nitrogen to total nitrogen ratio, showing a much higher amount of monocarbamate in the material.

The reaction or reactions may be conducted with or without the presence of a reaction solvent. A reaction solvent is generally employed whenever necessary to reduce the viscosity of the reaction product. These solvents should be stable and inert to the reactants and reaction product. Preferred solvents include aliphatic or aromatic hydrocarbons or aliphatic alcohols. Depending on the temperature of the reaction, the particular chloroformate used, the mol ratios and the particular amine, as well as the reactant concentrations, the reaction time may vary from less than 1 minute to 3 hours.

After the reaction has been carried out for a sufficient length of time, the reaction mixture may be subjected to extraction with a hydrocarbon-water or hydrocarbon-alcohol-water medium to free the product from any low-molecular-weight amine salts which have formed and any unreacted alkylene polyamines. The product may then be isolated by evaporation of the solvent. Small amounts of halogen may be present as the hydrohalide salt of the polyether aminocarbamates.

Depending on the particular application of the composition of this invention, the reaction may be carried out in the medium in which it will ultimately find use, e.g., polyether carriers or an oleophilic organic solvent or mixtures thereof and be formed at concentrations which provide a concentrate of a detergent composition. Thus, the final mixture may be in a form to be used directly for blending in lubricating oils.

Although the lubricating oil additive of the present invention has been described in terms of amine and poly(oxyalkylene) components coupled via a chloroformylation reaction utilizing phosgene, as is known to those of skill in the art, there are other methods of preparing carbamates which use other reactants. For example, the reaction of an isocyanate with an alcohol such as the hydroxycarbylpoly(oxyalkylene) alcohol described above also produces a carbamate. Monoisocyanato amines are produced, for example, by the methods of U.S. Pat. No. 3,644,490. Consequently, it is, for example, within the skill of the art to use a selected isocyanate-substituted amine or polyamine to react directly with said poly(oxyalkylene) alcohol to produce a carbamate within the scope of the present invention. This route may be exemplified by the reaction of $(CH_3)_2NCH_2CH_2N{=}C{=}O$ with a hydrocarbylpoly(oxyalkylene) alcohol to produce a carbamate characteristic of the present invention.

LUBRICATING OIL COMPOSITIONS

The lubricating oil compositions of the invention are useful for lubricating internal combustion engines. The lubricating oils not only lubricate the engine, but, because of their dispersancy properties, help maintain a high degree of cleanliness of the lubricated parts.

Suitable lubricating oils which can be used to prepare a lubricating oil composition or concentrate of this invention are oils of lubricating viscosity derived from petroleum or synthetic sources. The oils can be paraffinic, naphthenic, halo-substituted hydrocarbons, synthetic esters, polyethers, alkylbenzenes, or combinations thereof. Oils of lubricating viscosity have viscosities in the range of 35 to 50,000 SUS at 100° F., and more usually from about 50 to 10,000 SUS at 100° F. The amount of the aminocarbamate of this invention which is incorporated into the lubricating oil to provide the effective amount necessary for dispersancy varies widely with the particular aminocarbamate used as well as the use intended for the lubricating oil composition. Other conventional additives which can be used in combination with the poly(oxyalkylene) aminocarbamates of this invention include ashless dispersants such as the type disclosed in U.S. Pat. Nos. 3,172,892, 3,219,666, 3,381,022; neutral and basic calcium, barium and magnesium petrosulfonates or alkyl phenates; oxidation inhibitors, antifoam agents, viscosity index improvers, pour-point depressants, and the like, such as chlorinated wax, benzyldisulfide, sulfurized sperm oil, sulfurized terpene; phosphorus esters such as trihydrocarbon phosphites and phosphates; metal thiocarbamates such as zinc dioctyldithiocarbamate; metal phosphorus dithioates such as zinc dioctylphosphorodithioate; polyisobutene having an average molecular weight of 100,000; etc.

In general, the lubricating oil compositions will contain from about 0.01 to about 20 weight percent of said oil-soluble aminocarbamate. More usually, the lubricating oil composition of the invention will contain from about 0.5 to about 10 weight percent of the aminocarbamate and more usually from about 1 to about 8 weight percent of the aminocarbamate.

In a second embodiment of this invention, lubricating oil additive concentrates are provided comprising from about 90 to about 20 weight percent of an inert stable oleophilic solvent such as oil of lubricating viscosity and from about 10 to about 80 weight percent of the poly(oxyalkylene) aminocarbamates of this invention. Typically, the concentrates contain sufficient diluent to make them easy to handle during shipping and storage. Preferably, the diluent is an oil of lubricating viscosity so that the concentrate may be readily mixed with lubricating oils to prepare lubricating oil compositions. Suitable lubricating oils which can be used as diluents typically have viscosities in the range from about 35 to about 1000 Saybolt Universal Seconds (SUS) at 100° F., although any oil of lubricating viscosity can be used.

EXEMPLIFICATION

The following examples are presented to illustrate specific embodiments of the practice of this invention and should not be interpreted as limitations upon the scope of the invention.

EXAMPLE 1

Preparation of Alkylphenylpoly(oxybutylene) Alcohol

The experiment was carried out in dry glassware under an inert atmosphere. Potassium (1.17 g, 0.03 mol) was added to 26.34 g (0.1 mol) of a phenol alkylated with propylene tetramer. The mixture was stirred and heated to 50° C. for 24 hours until the potassium dissolved. The pot temperature was raised to 80° C. and 1,2-epoxybutane (215 ml, 2.5 mols) was added at a rate slow enough to prevent flooding of the condenser. The reaction was stirred and heated at reflux until the pot temperature reached 125° C. The product was extracted into 2 volumes of diethyl ether and washed with two volumes of 0.5 N HCl. Diethyl ether (250 ml) was added to the ethereal layer, and it was washed four times with 250-ml aliquots of water. The solvent was removed and the product was azeotroped with toluene to remove traces of water. A yield of 145 g of a viscous liquid of molecular weight approximately 1500 was obtained.

EXAMPLE 2

Reaction of Alkylphenylpoly(oxybutylene) Alcohol with Phosgene

Phosgene (14 ml, 0.198 mol) was condensed and transferred to a flask containing 150 ml of toluene. This mixture was cooled and stirred in an ice bath while the poly(oxybutylene) alcohol of Example 1 (140 g, 0.09 mol) was added dropwise. After the addition was complete, the ice bath was removed and the mixture was stirred for about 1 hour. An aliquot was taken, and the infra-red spectrum of its non-volatile residue showed a strong chloroformate absorption at 1785 $cm^{-1}$.

EXAMPLE 3

Reaction of Alkylphenylpoly(oxybutylene) Chloroformate with Amine

Ethylenediamine (41 ml, 0.61 mol) was stirred rapidly and cooled in an ice bath. The chloroformate of Example 2 was diluted with four volumes of toluene and added to the ethylenediamine at such a rate that the pot temperature did not exceed 30° C. After the addition was completed, the ice bath was removed and the mixture was stirred for about 1 hour.

The mixture was extracted into 500-ml of hot n-butanol and washed four times with 500-ml aliquots of hot water. The solvent was removed and the product was azeotroped with toluene to remove traces of water, giving 125 g of a viscous amber liquid of molecular weight about 1600. The product alkylphenylpoly(oxybutylene)ethylenediamine carbamate, i.e., alkylphenylpoly(oxybutylene)-N-(2-aminoethyl) carbamate, contained 1.20% by weight nitrogen and dispersed sludge at 200–400 ppm.

The poly(oxyalkylene) aminocarbamate of this invention was tested in an internal combustion engine to demonstrate its usefulness as a lubricating oil additive. In the test a Ford 6-cylinder engine of 240 cubic inch displacement (CID) was cycled through idle/cold/hot cycles according to the schedule set forth in the following Table I:

TABLE I

Operating Schedule
Ford 240CID 6 Cylinder Engine Test - 80 Hours

| Operating Mode | Manifold Vacuum In-Hq. | Coolant Temp. °F. | Oil Temp. °F. | Duration Hours | RPM |
|---|---|---|---|---|---|
| I | 13–15 | 135 | — | 0.25 | 600 |
| II | 6.0 | 135 | 175 | 2 | 2500 |
| III | 6.0 | 200 | 225 | 2 | 2500 |

Following 80 hours of operation, the engine is dismantled, and all parts are rated for sludge and varnish using standard Coordinating Research Council rating scales and procedures wherein varnish is rated on a scale of 0 to 10, with 10 being completely clean.

The following Table II gives a comparison of sludge and varnish ratings for two test runs. Run #1 used an SAE 30 base oil containing no dispersant or detergent additives. Run 2 used the same base oil with addition of the poly(oxybutylene) aminocarbamate of Example 3 at 4.5%wt. The fuel for both runs was a typical commercial unleaded gasoline with addition of tetraethyl lead at 0.5 g Pb/gal.

TABLE II

FORD 240 CID
ENGINE 4A CRANKCASE DEPOSIT TEST RESULTS

| | Run 1 SAE 30 Oil NC Dispersant | Run 2 SAE 30 Oil 4.5 Wt.%** |
|---|---|---|
| Varnish Ratings* & Piston Deposits | | |
| Cylinder Bore Varnish | 6.9 | 10 |
| Piston Skirt Varnish | 5.4 | 10 |
| Piston Underhead Varnish | 2.0 | 7.2 |
| Piston Pin Boss Varnish | 4.2 | 10 |
| Piston Ring Groove Filling, % | 43 | 6 |
| Oil Ring Plugging, % | 2 | 0 |
| Sludge Ratings* | | |
| Rocker Cover Sludge | 8.4 | 9.4 |
| Push Rod Cover Sludge | 8.5 | 9.1 |
| Push Rod Chamber Sludge | 8.8 | 9.5 |
| Timing Gear Cover Sludge | 8.5 | 9.9 |
| Oil Pan Sludge | 9.0 | 9.3 |

*0-10 scale, 10 = clean.
**Alkylphenylpoly(oxybutylene)-N-(2-aminoethyl)carbamate.

From the data, it is apparent that the hydrocarbylpoly(oxyalkylene) aminocarbamates are effective dispersant additives in lubricating oil compositions.

Although many specific embodiments of the invention have been described in detail, it should be understood that the invention is to be given the broadest possible interpretation within the terms of the following claims.

What is claimed is:

1. A lubricating oil composition comprising a major amount of an oil of lubricating viscosity, and a minor amount of a hydrocarbylpoly(oxyalkylene) aminocarbamate of molecular weight from about 600 to 10,000, and having at least one basic nitrogen atom; wherein said poly(oxyalkylene) moiety is composed of oxyalkylene units selected from 2 to 5 carbon oxyalkylene units of which at least a sufficient number are branched chain oxyalkylene units to render said carbamate soluble in said composition; and said hydrocarbyl group contains from 1 to about 30 carbon atoms.

2. The composition of claim 1 in which at least one basic nitrogen atom in said aminocarbamate is in a primary or secondary amino group.

3. The composition of claim 1 in which said hydrocarbylpoly(oxyalkylene) moiety consists of 1 to 2 hydrocarbylpoly(oxyalkylene) polymers.

4. The composition of claim 3 in which each said oxyalkylene units contains 3 to 4 carbon atoms.

5. The composition of claim 4 in which said oxyalkylene units are oxybutylene.

6. The composition of claim 1 in which said hydrocarbylpoly(oxyalkylene) moiety has a molecular weight of from about 500 to 5,000.

7. The composition of claim 1 in which said aminocarbamate has a molecular weight of about 1,200 to 5,000.

8. The composition of claim 1 in which said hydrocarbyl group contains from 2 to about 20 carbon atoms.

9. The composition of claim 1 in which said hydrocarbyl group is an alkylphenyl group.

10. The composition of claim 9 in which the alkyl in said alkylphenyl group is propylene tetramer.

11. The composition of claim 1 wherein the amine moiety of said aminocarbamate is derived from a polyamine having from 2 to 12 amine nitrogen atoms and from 2 to 40 carbon atoms with a carbon:nitrogen ratio between 1:1 and 10:1.

12. The composition of claim 11 in which said polyamine is a substituted polyamine with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C).

13. The composition of claim 11 in which said polyamine is a polyalkylene polyamine wherein the alkylene group contains from 2 to 6 carbon atoms and the polyamine contains 2 to 12 amine nitrogen atoms and 2 to 24 carbon atoms.

14. The composition of claim 13 in which said polyalkylene polyamine is selected from the group consisting of ethylene diamine, polyethylene polyamine, propylene diamine and polypropylene polyamine.

15. The composition of claim 11 in which said polyamine is ethylene diamine.

16. The composition of claim 1 in which said hydrocarbylpoly(oxyalkylene) aminocarbamate is butylpoly(oxypropylene)-N-(2-aminoethyl) carbamate.

17. The composition of claim 1 in which said hydrocarbylpoly(oxyalkylene) aminocarbamate is alkylphenylpoly(oxyisobutylene)-N-(2-aminoethyl) carbamate.

18. A lubricating oil composition comprising a major amount of an oil of lubricating viscosity and a minor amount of a compound of the formula:

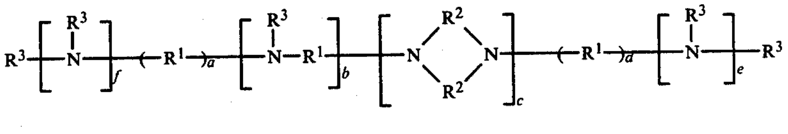

wherein two $R^3$ groups attached to the same nitrogen atom and taken together with said nitrogen atom may form a 5 or 6 membered saturated or unsaturated nitrogen heterocyclic radical; wherein said heterocyclic radical may be substituted with substituents selected from: (A) hydrogen, (B) hydrocarbyl groups of from 1 to 10 carbon atoms; (C) acyl groups of from 2 to 10 carbon atoms; and (D) monoketo, monohydroxy, mononitro, monocyano, lower alkyl and lower alkoxy derivatives of the substituents of (B) and (C); wherein the remaining $R^3$ groups are the same or different substituents selected from (A), (B), (C), (D) and poly(oxyalkylene) oxycarbonyl groups of the formula $R(OC_gH_{2g})_mO—C(O)—$ in which g is an integer from 2 to 5; j is an integer such that the molecular weight of the poly(oxyalkylene) group is about 500 to 5,000, and R is a hydrocarbyl group of from 1 to 30 carbon atoms, wherein the $R^1$ are the same or different alkylene, carbonyl, oxycarbonyl, or hydroxy-substituted alkylene radical of from 2 to 6 carbon atoms, and $R^2$ is carbonyl, alkylene carbonyl or alkylene of 2 to 4 carbon atoms with vicinal linkages; wherein at least one of the $R^3$ groups is said poly(oxyalkylene) oxycarbonyl group in which a sufficient number of oxyalkylene units, $(OC_gH_{2g})$, are branched chains $C_3$–$C_5$ oxyalkylene units to render said compound soluble in said lubricating oil composition; wherein $R^3$, $R^1$, and $R^2$ are selected such that at least one nitrogen atom is a basic nitrogen atom; and wherein a is 0 or 1, b is an integer 0 to 4, c is 0 or 1, d is 0 or 1, e is 0 or 1, f is 0 or 1 and equal to 1 when c is 0, and the sum f+b+2c+e is equal to or greater than 2.

19. The composition of claim 18 in which g is 3 or 4.

20. The composition of claim 19 in which f, a, and e are each equal to 1 and c and d are each 0.

21. The composition of claim 20 in which all the $R^3$ groups other than the poly(oxyalkylene) group are H.

22. The composition of claim 21 in which $R^1$ is propylene.

23. The composition of claim 21 in which $R^1$ is ethylene.

24. The composition of claim 21 in which R is an alkylphenyl group.

* * * * *

UNITED STATES PATENT AND TRADEMARK OFFICE
CERTIFICATE OF CORRECTION

PATENT NO. : 4,233,168

DATED : November 11, 1980

INVENTOR(S) : Robert A. Lewis and Lewis R. Honnen

It is certified that error appears in the above-identified patent and that said Letters Patent are hereby corrected as shown below:

Column 3, line 31, "amino nitrogen" should read --amine nitrogen--

Column 14, line 1, "$R\leftarrow OC_gH_{2g})_mO-C(O)-$" should read

--$R\leftarrow OC_gH_{2g})_jO-C(O)-$ --

Signed and Sealed this

*Third* Day of *March 1981*

[SEAL]

*Attest:*

RENE D. TEGTMEYER

*Attesting Officer* *Acting Commissioner of Patents and Trademarks*